United States Patent
Lin

(10) Patent No.: US 9,955,734 B2
(45) Date of Patent: May 1, 2018

(54) ELECTRONIC CIGARETTE FOR CONVENIENT INJECTION OF CIGARETTE LIQUID, MANUFACTURING METHOD THEREOF, AND CIGARETTE LIQUID INJECTION METHOD THEREOF

(71) Applicant: Guangrong Lin, Guangdong (CN)

(72) Inventor: Guangrong Lin, Guangdong (CN)

( * ) Notice: Subject to any disclaimer, the term of this patent is extended or adjusted under 35 U.S.C. 154(b) by 117 days.

(21) Appl. No.: 14/997,597

(22) Filed: Jan. 18, 2016

(65) Prior Publication Data
US 2016/0128385 A1    May 12, 2016

Related U.S. Application Data

(63) Continuation-in-part of application No. PCT/CN2014/092637, filed on Dec. 1, 2014.

(30) Foreign Application Priority Data

Jan. 15, 2014    (CN) .......................... 2014 1 0017542

(51) Int. Cl.
    *A24F 47/00*    (2006.01)
(52) U.S. Cl.
    CPC .......... *A24F 47/008* (2013.01); *A24F 47/002* (2013.01)
(58) Field of Classification Search
    CPC .... A24F 47/008; A61M 11/002; A61M 11/06; A61M 11/08; A61M 15/0035; A61M 15/0036; A61M 15/004
    See application file for complete search history.

(56) References Cited

U.S. PATENT DOCUMENTS

| | | | |
|---|---|---|---|
| 9,861,141 B1 * | 1/2018 | Liu | ........................ A24F 47/008 |
| 2010/0200008 A1 * | 8/2010 | Taieb | .................... A24F 47/008 131/360 |

(Continued)

FOREIGN PATENT DOCUMENTS

| | | | |
|---|---|---|---|
| CN | 202206877 U | | 5/2012 |
| CN | 202445134 U | * | 9/2012 |

(Continued)

OTHER PUBLICATIONS

Google Patents English translations of the following foreign patent documents: CN 202834037 U, CN 202834037 U, CN 203723443 U, WO 2012070107 A1, WO 2013089551 A1, WO 2015179002 A2.*

(Continued)

*Primary Examiner* — Seyed Masoud Malekzadeh
*Assistant Examiner* — Taryn Trace Willett

(57) ABSTRACT

The present invention relates to an electronic cigarette for convenient injection of cigarette liquid, manufacturing method thereof, and a method for injecting cigarette liquid into the electronic cigarette. A liquid injection hole is opened at a bottom of a liquid storage cup of the electronic cigarette, and the liquid injection hole is sealed by a sealing element which is self-closing once an injection device has been pulled out from the sealing element. The components of the electronic cigarette of the present invention can be assembled together first prior to the injection of cigarette liquid. Therefore, the problem of leakage and contamination of cigarette liquid during the manufacture of existing electronic cigarettes can be overcome. The automated injection of cigarette liquid can be carried out at places where the electronic cigarettes are sold.

6 Claims, 2 Drawing Sheets

(56) References Cited

U.S. PATENT DOCUMENTS

| | | | |
|---|---|---|---|
| 2011/0011396 A1* | 1/2011 | Fang | A24F 47/008 128/202.21 |
| 2011/0094523 A1* | 4/2011 | Thorens | A24F 47/008 131/194 |
| 2013/0192617 A1* | 8/2013 | Thompson | A24F 47/008 131/329 |
| 2013/0192618 A1* | 8/2013 | Li | A24F 47/008 131/329 |
| 2014/0196734 A1* | 7/2014 | Liu | A24F 47/008 131/329 |
| 2014/0332022 A1* | 11/2014 | Li | A24F 47/008 131/329 |
| 2015/0157053 A1* | 6/2015 | Mayor | A24F 47/008 131/329 |
| 2015/0196059 A1* | 7/2015 | Liu | H05B 3/06 131/329 |
| 2015/0257447 A1* | 9/2015 | Sullivan | A24F 47/008 131/329 |
| 2015/0272217 A1* | 10/2015 | Chen | A24F 47/008 131/329 |
| 2015/0351457 A1* | 12/2015 | Liu | A24F 47/008 131/328 |
| 2016/0286860 A1* | 10/2016 | Flayler | A24F 47/008 |
| 2016/0316820 A1* | 11/2016 | Liu | A24F 47/008 |
| 2017/0119060 A1* | 5/2017 | Li | A24F 47/008 |
| 2017/0172210 A1* | 6/2017 | Bright | A24F 47/008 |

FOREIGN PATENT DOCUMENTS

| | | | | |
|---|---|---|---|---|
| CN | 202603604 U | | 12/2012 | |
| CN | 202834037 U | * | 3/2013 | |
| CN | 203723443 U | * | 7/2014 | |
| WO | WO 2012070107 A1 | * | 5/2012 | A24F 47/00 |
| WO | WO 2013089551 A1 | * | 6/2013 | A61M 15/06 |
| WO | WO 2015179002 A2 | * | 11/2015 | A24F 47/008 |

OTHER PUBLICATIONS

International Search Report of PCT Patent Application No. PCT/CN2014/092637 dated Mar. 4, 2015.

1st Office Action of counterpart Chinese Patent Application No. 201410017542.X dated Jul. 22, 2015.

3rd Office Action of counterpart Chinese Patent Application No. 201410017542.X dated Nov. 24, 2015.

* cited by examiner

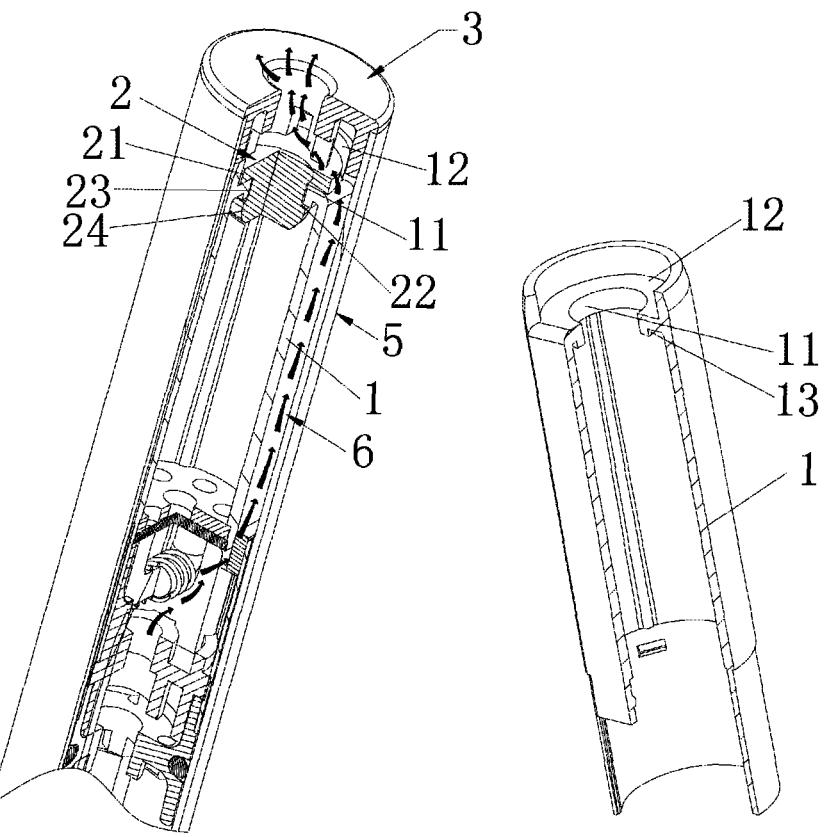
Figure 2
Figure 3
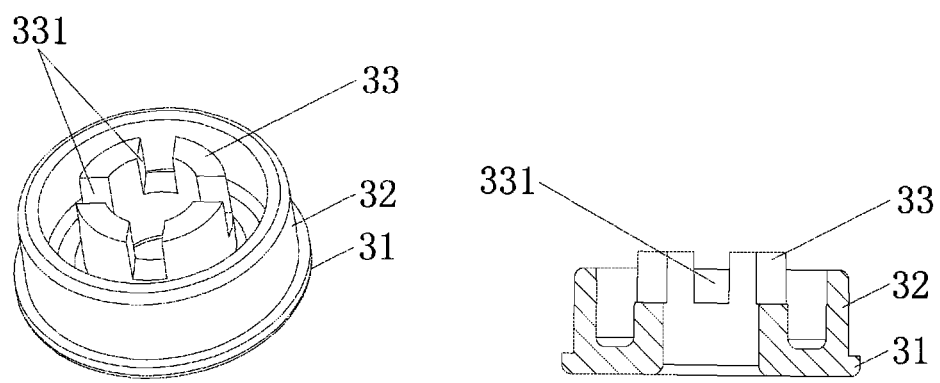
Figure 4
Figure 5

ELECTRONIC CIGARETTE FOR CONVENIENT INJECTION OF CIGARETTE LIQUID, MANUFACTURING METHOD THEREOF, AND CIGARETTE LIQUID INJECTION METHOD THEREOF

CROSS-REFERENCE TO RELATED APPLICATIONS

This present application is a Continuation-in-Part Application of PCT application No. PCT/CN2014/092637 filed on Dec. 1, 2014, which claims the benefit of Chinese Patent Application No. 201410017542.X filed on Jan. 15, 2014, the contents of which are hereby incorporated by reference.

FIELD OF THE INVENTION

The present invention relates to an electronic cigarette for convenient injection of cigarette liquid, a method for manufacturing the electronic cigarette, and a method for injecting cigarette liquid into the electronic cigarette.

BACKGROUND OF THE INVENTION

Cigarette liquid is usually injected into a liquid storage cup of an existing electronic cigarette prior to the assembling of components of the electronic cigarette. Such injection manner is not convenient for manufacturing the electronic cigarette, because the injected cigarette liquid is prone to leakage from the liquid storage cup of the electronic cigarette and is easily contaminated.

SUMMARY OF THE INVENTION

In order to overcome the problem of leakage and contamination of cigarette liquid during the manufacture of existing electronic cigarettes, the present invention aims to provide an electronic cigarette for convenient injection of cigarette liquid. The components of the electronic cigarette of the present invention are assembled prior to the injection of cigarette liquid. The present invention also aims to provide a method for efficiently and automatically manufacturing the electronic cigarette. The present invention also aims to provide a method for injecting cigarette liquid into the electronic cigarette. By using the injection method of the present invention, the injection of cigarette liquid can be carried out at places where the electronic cigarettes are sold.

The technical solution of the present invention is an electronic cigarette for convenient injection of cigarette liquid, comprising a mouthpiece cap, a liquid storage cup, a vaporizing assembly, and a battery assembly; wherein a liquid injection hole is opened at a bottom of the liquid storage cup; and the liquid injection hole is sealed by a sealing element which is self-closing once an injection device has been pulled out from the sealing element.

Preferably, the bottom of the liquid storage cup is concaved to form a cavity; the liquid injection hole is a through-hole opened at a centre of a bottom wall of the cavity; a wall of the liquid injection hole is protruded towards an interior of the liquid storage cup to form a protrusion; the sealing element has a ⊥ shaped cross section, the sealing element consists of a top portion, a bottom portion, a neck portion connecting the top portion to the bottom portion, and a circular recess formed between the top portion and the bottom portion; the protrusion of the wall of the liquid injection hole is snap-fitted into the circular recess of the sealing element.

Preferably, a diameter of the top portion of the sealing element is large than that of the bottom portion of the sealing element.

Preferably, the sealing element is made of silicone or rubber.

Preferably, the mouthpiece cap consists of a mouth-contacting piece having an extension portion and an opening, the extension portion being arranged on a mouth portion of a shell of the electronic cigarette, the opening being opened at a centre of the mouth-contacting piece; an outer tubular neck and an inner tubular neck that are protruded perpendicularly from a surface of the mouth-contacting piece and are concentrically nested, axes of the outer tubular neck and the inner tubular neck passing through a center of a circumference of the mouth-contacting piece, an end surface of the inner tubular neck being pressed against the sealing element; and four grooves uniformly spaced in the inner tubular neck; wherein a vapor-flow passage comprises an annulus formed between the outer tubular neck and the inner tubular neck, said four grooves, and the opening.

Preferably, the sealing element has a T-shaped cross section, the sealing element consists of a cylinder portion and an extension portion extending radially from a top surface of the cylinder portion; the cylinder portion is inserted into the liquid injection hole.

Another embodiment of the present invention provides a method for manufacturing the electronic cigarette comprising:

assembling the liquid storage cup and assembling the vaporizing assembly;

assembling the battery assembly; and assembling the liquid storage cup, the vaporizing assembly, the battery assembly, the mouthpiece cap, and a shell of the electronic cigarette to form the electronic cigarette;

wherein the step of assembling the liquid storage cup and assembling the vaporizing assembly comprises the steps of:

concaving the bottom of the liquid storage cup to form a cavity, opening the liquid injection hole at a centre of a bottom wall of the cavity, protruding a wall of the liquid injection hole towards an interior of the liquid storage cup to form a protrusion;

manufacturing the sealing element having a ⊥ shaped cross section, the sealing element consisting of a top portion, a bottom portion, a neck portion connecting the top portion to the bottom portion, and a circular recess formed between the top portion and the bottom portion; and snap-fitting the protrusion of the wall of the liquid injection hole into the circular recess of the sealing element.

Another embodiment of the present invention provides a method for injecting cigarette liquid into the electronic cigarette, comprising the steps of:

opening the liquid injection hole at a centre of the bottom of the liquid storage cup, manufacturing the sealing element which is used for sealing the liquid injection hole;

inserting the sealing element tightly into the liquid injection hole;

fixing the mouthpiece cap to a mouth portion of a shell of the electronic cigarette;

inserting the injection device into an opening of the mouthpiece cap and the sealing element to inject cigarette liquid into the liquid storage cup; and pulling the injection device out from the sealing element, the sealing element being self-closed once the injection device has been pulled out from the sealing element.

Preferably, the injection device is an injection needle.

The advantages of the electronic cigarette of the present invention are as follows. (1) A liquid injection hole is opened at a bottom of the liquid storage cup, and the liquid injection hole is sealed by a sealing element which is self-closing once an injection device has been pulled out from the sealing element, in this way, all of the components of the electronic cigarette of the present invention can be assembled together first prior to the injection of cigarette liquid. (2) The problem of leakage and contamination of cigarette liquid during the manufacture of electronic cigarettes can be overcome. (3) The electronic cigarette of the present invention can be efficiently and automatically manufactured, the injection of cigarette liquid can be carried out at places where the electronic cigarettes are sold.

BRIEF DESCRIPTION OF THE DRAWINGS

FIG. 2 shows a liquid injection hole and a sealing element of the electronic cigarette of the present invention.

FIG. 3 is a schematic view of a liquid storage cup of the electronic cigarette of the present invention, the liquid storage cup being partially sectioned.

FIG. 4 is a schematic view of a mouthpiece cap of the electronic cigarette of the present invention.

FIG. 5 is a cross-sectional view of a mouthpiece cap of the electronic cigarette of the present invention.

Figure 1:
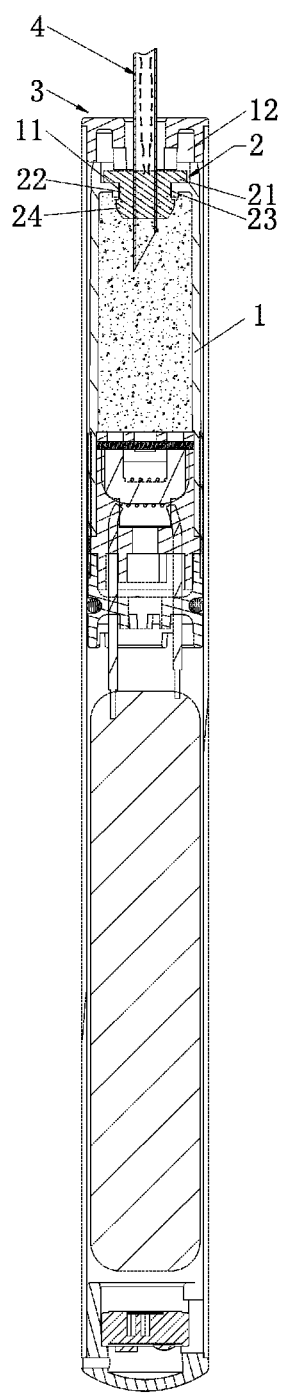
FIG. 1 is a cross-sectional view of an assembled electronic cigarette of the present invention, an injection device being inserted into a liquid storage cup of the electronic cigarette to inject cigarette liquid into the liquid storage cup.

LIST OF REFERENCE NUMERALS OF MAIN COMPONENTS 1 liquid storage cup
11 liquid injection hole
12 cavity
13 protrusion
2 sealing element
21 top portion
22 neck portion
23 circular recess
24 bottom portion
3 mouthpiece cap
31 mouth-contacting piece
32 outer tubular neck
33 inner tubular neck
331 groove
4 injection device
5 shell
6 vapor-flow passage

DETAILED DESCRIPTION OF ILLUSTRATED EMBODIMENTS

Detailed embodiments of the present invention are described below in conjunction with drawings.

As shown in FIG. 2, an electronic cigarette for convenient injection of cigarette liquid of the present invention comprises a mouthpiece cap 3, a liquid storage cup 1, a vaporizing assembly, and a battery assembly. A liquid injection hole 11 is opened at a bottom of the liquid storage cup 1; and the liquid injection hole 11 is sealed by a sealing element 2 which is self-closing once an injection device 4 has been pulled out from the sealing element 2.

As shown in FIG. 2, the sealing element 2 is made of silicone or rubber. The sealing element 2 has a ⊥ shaped cross section, the sealing element 2 consists of a top portion 21, a bottom portion 24, a neck portion 22 connecting the top portion 21 to the bottom portion 24, and a circular recess 23 formed between the top portion 21 and the bottom portion 24.

As shown in FIGS. 1-2, a diameter of the top portion 21 of the sealing element 2 is large than that of the bottom portion 24 of the sealing element 2.

In another embodiment of the present invention, the sealing element 2 has a T-shaped cross section (not shown in the figures), the sealing element 2 consists of a cylinder portion, and an extension portion extending radially from a top surface of the cylinder portion; the cylinder portion is inserted into the liquid injection hole 11.

As shown in FIGS. 4-5, the mouthpiece cap 3 consists of: a mouth-contacting piece 31 having an extension portion and an opening, the extension portion being arranged on a mouth portion of a shell 5 of the electronic cigarette, the opening being opened at a centre of the mouth-contacting piece 31; an outer tubular neck 32 and an inner tubular neck 33 that are protruded perpendicularly from a surface of the mouth-contacting piece 31 and are concentrically nested, axes of the outer tubular neck 32 and the inner tubular neck 33 passing through a center of a circumference of the mouth-contacting piece 31, a height of the inner tubular neck 33 being higher than that of the outer tubular neck 32, an end surface of the inner tubular neck 33 being pressed against the sealing element 2; and four grooves 311 uniformly spaced in the inner tubular neck 33. A vapor-flow passage 6 comprises an annulus formed between the outer tubular neck 32 and the inner tubular neck 33, said four grooves 311, and the opening.

As shown in FIG. 3, the bottom of the liquid storage cup 1 is concaved to form a cavity 12. A wall of the liquid injection hole 11 is protruded towards an interior of the liquid storage cup 1 to form a protrusion 13.

As shown in FIG. 2, the protrusion 13 of the wall of the liquid injection hole 11 is snap-fitted into the circular recess 23 of the sealing element 2.

Referring to FIGS. 1-5, a method for manufacturing the electronic cigarette comprises the steps of:
(1) assembling the liquid storage cup 1 and assembling the vaporizing assembly;
(2) assembling the battery assembly; and
(3) assembling the liquid storage cup 1, the vaporizing assembly, the battery assembly, the mouthpiece cap 3, and the shell 5 of the electronic cigarette to form the electronic cigarette.

Wherein the step of assembling the liquid storage cup 1 and assembling the vaporizing assembly comprises the steps of:
(1.1) concaving the bottom of the liquid storage cup 1 to form the cavity 12, opening the liquid injection hole 11 at a centre of a bottom wall of the cavity 12, protruding the wall of the liquid injection hole 11 towards the interior of the liquid storage cup 1 to form the protrusion 13;
(1.2) manufacturing the sealing element 2 having a ⊥ shaped cross section, the sealing element 2 consisting of a top portion 21, a bottom portion 24, a neck portion 22 connecting the top portion 21 to the bottom portion 24, and a circular recess 23 formed between the top portion 21 and the bottom portion 24; and
(1.3) snap-fitting the protrusion 13 of the wall of the liquid injection hole 11 into the circular recess 23 of the sealing element 2.

Referring to FIGS. 1-5, a method for injecting cigarette liquid into the electronic cigarette comprises the steps of:

(1) opening the liquid injection hole 11 at a centre of a bottom wall of the cavity 12, manufacturing the sealing element 2 which is used for sealing the liquid injection hole 11;

(2) inserting the sealing element 2 tightly into the liquid injection hole 11 to allow the protrusion 13 of the wall of the liquid injection hole 11 to be snap-fitted into the circular recess 23 of the sealing element 2;

(3) fixing the mouthpiece cap 3 to the mouth portion of the shell 5 of the electronic cigarette;

(4) inserting the injection device 4 into the opening of the mouthpiece cap 3 and the sealing element 2 to inject cigarette liquid into the electronic cigarette; and (5) pulling the injection device 4 out from the sealing element 2, the sealing element 2 being self-closed once the injection device 4 has been pulled out from the sealing element 2.

All the above are the preferred embodiments of the present invention, and the invention is intended to cover various modifications and equivalent arrangements included within the scope of the invention.

What is claimed is:

1. An electronic cigarette for convenient injection of cigarette liquid, comprising a mouthpiece cap, a liquid storage cup, a vaporizing assembly, and a battery assembly, wherein:
    a liquid injection hole is opened at a bottom of the liquid storage cup; and
    the liquid injection hole is sealed by a sealing element which is self-closing once an injection device has been pulled out from the sealing element;
    the bottom of the liquid storage cup is concaved to form a cavity;
    the liquid injection hole is a through-hole opened at a center of a bottom wall of the cavity;
    a wall of the liquid injection hole is protruded towards an interior of the liquid storage cup to form a protrusion;
    the sealing element has an I-shaped cross section, the sealing element consists of a top portion, a bottom portion, a neck portion connecting the top portion to the bottom portion, and a circular recess formed between the top portion and the bottom portion;
    the protrusion of the wall of the liquid injection hole is snap-fitted into the circular recess of the sealing element;
    wherein the mouthpiece cap consists of:
    a mouth-contacting piece having an extension portion and an opening, the extension portion being arranged on a mouth portion of a shell of the electronic cigarette, the opening being opened at a center of the mouth-contacting piece;
    an outer tubular neck and an inner tubular neck that are protruded perpendicularly from a surface of the mouth-contacting piece and are concentrically nested, axes of the outer tubular neck and the inner tubular neck passing through a center of a circumference of the mouth-contacting piece, an end surface of the inner tubular neck being pressed against the sealing element; and
    four grooves uniformly spaced in the inner tubular neck;
    wherein a vapor-flow passage comprises an annulus formed between the outer tubular neck and the inner tubular neck, said four grooves, and the opening.

2. The electronic cigarette for convenient injection of cigarette liquid according to claim 1, wherein a diameter of the top portion of the sealing element is larger than that of the bottom portion of the sealing element.

3. The electronic cigarette for convenient injection of cigarette liquid according to claim 1, wherein the sealing element is made of silicone or rubber.

4. A method for manufacturing the electronic cigarette according to claim 1, comprising:
    assembling the liquid storage cup and assembling the vaporizing assembly;
    assembling the battery assembly; and
    assembling the liquid storage cup, the vaporizing assembly, the battery assembly, the mouthpiece cap, and a shell of the electronic cigarette to form the electronic cigarette;
    wherein the step of assembling the liquid storage cup and assembling the vaporizing assembly comprises the steps of:
    concaving the bottom of the liquid storage cup to form a cavity, opening the liquid injection hole at a centre of a bottom of the cavity, protruding a wall of the liquid injection hole towards an interior of the liquid storage cup to form a protrusion;
    manufacturing the sealing element having an I-shaped cross section, the sealing element consisting of a top portion, a bottom portion, a neck portion connecting the top portion to the bottom portion, and a circular recess formed between the top portion and the bottom portion; and
    snap-fitting the protrusion of the wall of the liquid injection hole into the circular recess of the sealing element.

5. A method for injecting cigarette liquid into the electronic cigarette according to claim 1, comprising:
    opening the liquid injection hole at a centre of the bottom of the liquid storage cup, manufacturing the sealing element which is used for sealing the liquid injection hole;
    inserting the sealing element tightly into the liquid injection hole;
    fixing the mouthpiece cap to a mouth portion of a shell of the electronic cigarette;
    inserting the injection device into an opening of the mouthpiece cap and the sealing element to inject cigarette liquid into the liquid storage cup; and
    pulling the injection device out from the sealing element, the sealing element being self-closed once the injection device has been pulled out from the sealing element.

6. The method for injecting cigarette liquid according to claim 5, wherein the injection device is an injection needle.

* * * * *